United States Patent [19]
Schlom et al.

[11] Patent Number: 5,892,019
[45] Date of Patent: Apr. 6, 1999

[54] PRODUCTION OF A SINGLE-GENE-ENCODED IMMUNOGLOBULIN

[75] Inventors: Jeffrey Schlom, Potomac; Syed V. S. Kashmiri; Liming Shu, both of Gaithersburg, all of Md.

[73] Assignee: The United States of America, as represented by The Department of Health and Human Services, Washington, D.C.

[21] Appl. No.: 299,999

[22] Filed: Sep. 1, 1994

Related U.S. Application Data

[63] Continuation-in-part of Ser. No. 547,336, Jul. 2, 1990, Pat. No. 5,512,443, which is a continuation of Ser. No. 73,685, Jul. 15, 1987, abandoned.

[51] Int. Cl.$^6$ .......................... C07K 19/00; C12N 15/13; C07H 21/04
[52] U.S. Cl. .................................. 536/23.53; 424/130.1; 435/69.1; 435/69.7; 435/320.1; 435/344; 530/387.3
[58] Field of Search .............................. 530/387.1, 387.3, 530/387.7, 388.22, 388.3, 388.4, 388.73, 388.8, 866, 867; 536/23.53; 435/69.1, 69.7, 91.1, 240.1, 240.27, 252.3, 320.1, 254.1, 255.1

[56] References Cited

U.S. PATENT DOCUMENTS 4,522,918   6/1985   Schlom et al. .
4,612,282   9/1986   Schlom et al. .
4,946,778   8/1990   Ladner et al. .

FOREIGN PATENT DOCUMENTS

WO 89/07142   8/1989   WIPO .
WO 94/09817   5/1994   WIPO .

OTHER PUBLICATIONS

Traunecker et al. EMBO J. 10(12):3655–3659 (1991).
ATCC, *Catalogue of Cell Lines & Hybridomas*, 7th edition, 1992, pp. 377, 415 and 436.
Hutzell et al., "Generation and Characterization of a Recombinant/Chimeric B72.3 (Human $\gamma_1$)," *Cancer Res.* 51:181–189 (Jan. 1, 1991).
Milenic et al., "Construction, binding Properties, Metabolism and Tumor Targeting of a Single–Chain Fv Derived from the Pancarcinoma Monoclonal Antibody CC49," *Cancer Research*, 51:6363–6371, (Dec. 1, 1991).
Yokota et al., "Rapid Tumor Penetration of a Single–Chain Fv and Comparison with Other Immunoglobulin Forms," *Cancer Res.* 52:3402–3408 (Jun., 1992).
Hand et al., "Comparative Biological Properties of a Recombinant Chimeric Anti–Carcinoma mAb and a Recombinant Aglycosylated Variant," *Cancer Immunol. Immunother.* 35:165–174 (1992).
Tsang et al., "A Human T Cell Line Engineered to Secrete Chimeric Monoclonal Antibody," *J. Immunother.* 13:143–152 (1993).

Slavin–Chiorini et al., "Biologic Properties of a $C_H2$ Domain–Deleted Recombinant Immunoglobulin," *Int. J. Cancer* 53:97–103 (1993).
Shu et al. "Secretion of a single–gene–encoded immunoglobulin from myeloma cells," *Proc. Natl Acad. Sci. USA*, 90:7995–7999 (Sep., 1993).
Kashmiri "Secretion of Single–Gene–Encoded Novel Immunoglobulin Molecules from Myeloma Cells," *4th Ann. IBC Antibody Engineering Mtg.*, Coronado, CA (Dec., 1993).
Kashmiri et al., "A Novel Single–Gene–Encoded Single–Chain Immunoglobulin Molecule with Effector Functions," *AACR Abstract*, San Francisco, CA (Apr., 1994).
Kashmiri "Novel Single Chain Antibodies Encoded by Single Genes," *Artificial Antibodies & Enzymes*, San Diego, CA (Sep., 1994).
Kashmiri et al. "Single–gene–encoded novel single–chain antibodies with anti–tumor cytolytic activity," *XVI Int'l Cancer Congress*, New Delhi, India (Oct.–Nov. 1994).
Colcher et al., "A Spectrum of Monoclonal Antibodies Reactive with Human Mammary Tumor Cells," *Proc. Natl. Acad. Sci. USA* 78:3199–3203 (May, 1981).
Johnson et al., "Analysis of a Human Tumor Associated Glycoprotein (TAG–72) Identified by Monoclonal Antibody B72.3," *Cancer Res.* 46:850–857 (Feb., 1986).
Muraro et al., "Generation and Characterization of B72.3 Second Generation Monoclonal Antibodies Reactive with Tumor–associated Glycoprotein 72 Antigen," *Cancer Res.* 48:4588–4596 (Aug. 15, 1988).

(List continued on next page.)

*Primary Examiner*—Frank C. Eisenschenk
*Attorney, Agent, or Firm*—Morgan & Finnegan, L.L.P.

[57] ABSTRACT

Construction of a single gene encoding a signal-chain immunoglobulin-like molecule is described. This single-gene approach circumvents inefficiencies inherent in delivering two genes into a mammalian cell and in the assembly of a functional immunoglobulin molecule. It also facilitates ex vivo transfection of cells for gene-therapy protocols. The single-chain protein comprises the heavy- and light-chain variable ($V_H$ and $V_L$) domains of a monoclonal antibody covalently joined through a short linker peptide, while the carboxyl end of a V domain is linked to the amino terminus of a human constant region such as $\gamma 1$ Fc, through the hinge region. The single-chain protein assembles into a dimeric molecule of ≈120 kDa and is secreted into the culture fluid. The single-chain immunoglobulin-like protein shows similar antigen binding affinity to that of chimeric or parental antibody and mediates ADCC. This single-gene construct approach provides a way of generating an immunoglobulin-like molecule which retains the specificity, binding properties, and cytolytic activity of a parental monoclonal antibody, and thus is a useful therapeutic and diagnostic reagent against a range of antigens, such as human carcinomas.

28 Claims, 4 Drawing Sheets

OTHER PUBLICATIONS

Colcher et al., "Radioimmunolocalization of Human Carcinoma Xenografts with B72.3 Second Generation Monoclonal Antibodies," *Cancer Res.* 48:4597–4603 (Aug. 15, 1988).

Huston et al., "Protein Engineering of Antibody Binding Sites: Recovery of Specific Activity in an Anti–Digoxin Single–Chain Fv Analogue Produced in *Escherichia coli*," *Proc. Natl. Acad. Sci. USA* 85:5879–5883 (Aug., 1988).

Bird et al., "Single–Chain Antigen–Binding Proteins," *Science*, 242:423–426, (Oct. 21, 1988).

Molinolo et al., "Enhanced Tumor Binding Using Immunohistochemical Analyses by Second Generation Anti–Tumor–associated Glycoprotein 72 Monoclonal Antibodies versus Monoclonal Antibody B72.3 in Human Tissue," *Cancer Res.* 50:1291–1298 (Feb. 15, 1990).

Primus et al. "Chimeric B72.3 Mouse/Human (IgG1) Antibody Directs the Lysis of Tumor Cells by Lymphokine–Activated Killer Cells," *Cancer Immunol. Immunother.* 31:349–357 (1990).

Oi et al, "Chimeric Antibodies", *BioTechniques,* vol. 4, No. 3, (1986), pp. 214–221.

Jones et al, "Replacing the complementarity–determining regions in a human antibody with those from a mouse", *Nature,* vol. 321, May 1986, pp. 522–525.

Rice et al, "Regulated expression of an immunoglobulin k gene introduced into a mouse lymphoid cell line", *Proc. Natl. Acad. Sci USA,* vol. 79, pp. 7862–7865, Dec. 1982.

Kurokawa et al, "Expression of human immunoglobulin E t chain cDNA in *E. coli*", *Nucleic Acids Research,* vol. 11, No. 10, 1983, pp. 3077–3085.

Oi et al, "Immunoglobulin gene expression in transformed lymphoid cells", *Proc. Natl. Acad. Sci. USA,* vol. 80, pp. 825–829, Feb. 1983.

Boss et al, "Assembly of functional antibodies from immunoglobulin heavy and light chains synthesized in *E. coli*", *Nucleic Acids Research,* vol. 12, No. 9, 1984, pp. 3791–3806.

Boulianne et al, "Production of functional chimaeric mouse/human antibody", *Nature,* vol. 312, No. 13, Dec. 1984, pp. 643–646.

Cabilly et al, "Generation of antibody activity from immunoglobulin polypeptide chains produced in *Escherichia coli*", *Proc. Natl. Acad. Sci. USA,* vol. 81, pp. 3273–3277, Jun. 1984.

Kenten et al, "Properties of a human immunoglobulin E–chain fragment synthesized in *Escherichia coli*", *Proc. Natl. Acad. Sci. USA,* vol. 81, pp. 2955–2959, May 1984.

Liu et al, "Expression of a biologically active fragment of human IgE E chain in *Escherichia coli*", *Proc. Natl. Acad. Sci. USA,* vol. 81, pp. 5369–5373, Sep. 1984.

Morrison et al, "Chimeric human antibody molecules: Mouse antigen–binding domains with human constant region domains", *Proc. Natl. Acad. Sci. USA,* vol. 81, pp. 6851–6855, Nov. 1984.

Neuberger et al, "Recombinant antibodies possessing novel effector functions", *Nature,* vol. 312, No. 13, Dec. 1984, pp. 604–608.

Potter et al, "Enhancer–dependent expression of human K immunoglobulin genes introduced into mouse pre–B lymphocytes by electroporation", *Proc. Natl. Acad. Sci. USA,* vol. 81, pp. 7161–7165, Nov. 1984.

Neuberger et al, "A hapten–specific chimaeric IgE antibody with human physiological effector function", *Nature,* vol. 314, No. 21, Mar. 1985, pp. 268–270.

Sahagan et al, "A Genetically Engineered Murine/Human Chimeric Antibody Retains Specificity for Human Tumor––Associated Antigen", *The Journal of Immunology,* vol. 137, No. 3, pp. 1066–1074, Aug. 1986.

Sun et al, "Chimeric Antibodies with 17–1A–Derived Variable and Human Constant Regions", *Hybridoma,* vol. 5, Suppl. 1, 1986, pp. S17–S20.

Sun et al, "Chimeric antibody with human constant regions and mouse variable regions directed against carcinoma–associated antigen 17–1A", *Proc. Natl. Acad. Sci. USA,* vol. 84, pp. 214–218, Jan. 1987.

PRODUCTION OF A SINGLE-GENE-ENCODED IMMUNOGLOBULIN

This application is a continuation-in-part of U.S. Ser. No. 07/547,336 filed Jul. 2, 1990, issued U.S. Pat. No. 5,512,443 on Apr. 30, 1996, which is a continuation of U.S. Ser. No. 07/073,685 filed Jul. 15, 1987, now abandoned.

BACKGROUND OF THE INVENTION

Single-chain immunoglobulin binding fragments, or sFv, are made up of the heavy chain variable ($V_H$) and light-chain variable ($V_L$) domains joined together through a short linker peptide. The sFv protein carries the antigen binding site, which confers binding specificity on the molecule. These molecules have been found to have an extremely rapid plasma and whole-body clearance rate in mice and rhesus monkeys (see, e.g., Milenic et al., *Cancer Res.* 51:6363–6371 (1991)). The sFv shows more rapid tumor penetration and more even distribution throughout the tumor mass (Yokota et al., *Cancer Res.* 52:3402–3408 (1992)) than a corresponding chimeric murine-human immunoglobulin. Recent studies have also shown, however, that the sFv and Fab' forms have lower equilibrium association constants ($K_a$) than the dimeric parental forms of the molecule; this, along with rapid clearance, has manifested itself in a lower percent injected dose per gram of sFv being deposited in a tumor site.

The sFv molecule per se, however, will not be sufficient for therapeutic use in its native (unconjugated) form. The cytolytic functions, such as ADCC and complement-dependent cytotoxicity, reside in the Fc region, which is exclusively made up of the constant-region domains of the heavy chain ($C_H$ domains). For a native antibody to be therapeutically effective against tumors it must, therefore, carry both antigen binding site and the Fc region. It has also been shown that N-linked glycosylation of Asn-297 within the $C_H2$ domain is critical for binding to the Fc receptor of the human effector cells and is necessary for ADCC activity (Tao et al., *J. Immunol.* 143:2595–2601 (1989), Dorai et al., *Hybridoma* 10:211–217 (1991) and Horan Hand et al., *Cancer Immunol. Immunother.* 35:165–174 (1992)). Fc-linked glycosyl residues are also implicated in complement fixation (Tao et al., *J. Immunol.* 143:2595–2601 (1989)). Since glycosylation of the Fc region is a characteristic of the eukaryotic system, an unconjugated antibody for therapeutic application must be produced in eukaryotic cells.

Transfection of eukaryotic cells remains highly inefficient, at best. It is all the more inefficient to develop a transfectant synthesizing a functional antibody molecule encoded by two separate genes. Currently, it is not feasible to carry out ex vivo introduction of two immunoglobulin genes simultaneously in a significant percentage of a cell population for reintroduction of the transfected cells into the host for genetic immunotherapy.

Monoclonal antibody (mAb) CC49, a murine IgG1, is a second-generation monoclonal of mAb B72.3 (Colcher et al., *Proc. Natl. Acad. Sci. USA* 78:3199–3203 (1981)), which reacts with the tumor-associated glycoprotein TAG-72 (Johnson et al., *Cancer Res.* 46:850–857 (1986)) expressed on a variety of carcinomas. Murine CC49 was developed by immunizing mice with TAG-72 purified by B72.3 affinity chromatography. Compared with B72.3, CC49 has a higher antigen binding affinity (Muraro et al., *Cancer Res.* 48:4588–4596 (1988)) and targets human colon carcinoma xenografts in mice more efficiently and reduces the growth of the xenograft with greater efficacy (Colcher et al., *Cancer Res.* 48:4597–4603 (1988) and Molinolo et al., *Cancer Res.* 50:1291–1298 (1990)). Chimeric B72.3 with a human γ1 constant region has been shown to efficiently mediate antibody-dependent cellular cytotoxicity (ADCC). Results from ongoing clinical trials suggest that murine CC49 is a useful clinical reagent for targeting human colorectal carcinoma lesions.

While the single-chain sFv form of CC49 has been shown to have important diagnostic use, what is needed in the art is a means to provide therapeutically useful single chain binding molecules of CC49 and other clinically useful antibodies. Quite surprisingly, the present invention fulfills this and other related needs.

SUMMARY OF THE INVENTION

The present invention provides an isolated polynucleotide molecule which codes for a single chain immunoglobulin-like polypeptide having binding affinity for an antigen. The immunoglobulin-like polypeptide comprises a first polypeptide comprising the binding portion of the light chain variable region of an antibody or substantially all of the light chain variable region; a second polypeptide comprising the binding portion of the heavy chain variable region of an antibody or substantially all of the variable region; at least one peptide linker linking said first and second polypeptides; and a third polypeptide comprising the constant region domains CH2 and CH3. The single-gene-encoded immunoglobulin-like polypeptide has binding affinity for the antigen and is capable of forming an immunoglobulin-like dimer. The constant region effector functions associated with the CH2 and CH3 domains include mediation of antibody-dependent cellular cytotoxicity against cells which express the antigen of interest. The peptide linker is not necessarily from an antibody, and links the first and second polypeptides into the single chain polypeptide.

Thus, according to the present invention that single chain polypeptide encoded by the polynucleotide molecule may comprise, in sequence: (i) an N-terminal polypeptide from the light chain variable region of an antibody; (ii) a peptide linker; (iii) a C-terminal polypeptide from the heavy chain variable region of an antibody; and (iv) a heavy chain constant region domain. Alternatively, the elements may be arranged in the sequence: (i) an N-terminal polypeptide from the heavy chain variable region of an antibody; (ii) a peptide linker; (iii) a C-terminal polypeptide from the heavy chain variable region of an antibody; and (iv) the heavy chain constant region domain. In preferred embodiments the heavy chain constant region domains are the CH2 and CH3 domains, and are preferably substantially human when the polypeptide is intended for use in humans.

In preferred embodiments the polynucleotide molecule of the invention encode a single-chain immunoglobulin-like polypeptide which forms a dimer and binds to a tumor associated antigen, a viral or bacterial antigen, a lymphocyte associate antigen, or a cell adhesion molecule or ligand thereof. Particularly preferred as a tumor associated antigen is TAG-72.

Also provided as an aspect of the present invention is a replicable cloning or expression vehicle, such as a plasmid or retrovirus, comprising the polynucleotide molecule which expresses the polypeptide capable of forming the immunoglobulin-like dimer, and host cells transformed with the expression vehicle. Such host cells are mammalian, bacterial, yeast or other fungal cell, but preferably are eucaryotic, and more preferably a myeloma cell line.

In another embodiment the invention provides methods for producing a single chain immunoglobulin-like polypeptide having binding affinity for an antigen and capable of forming a dimer. The method comprises providing an isolated polynucleotide molecule coding for the polypeptide, transforming a host cell with the polynucleotide molecule, expressing the polynucleotide molecule in the host said host, and recovering the polypeptide having the binding affinity for the antigen. The immunoglobulin-like polypeptide so recovered can subsequently be subjected to further separation and purification.

Accordingly, in another aspect the invention further provides an immunoglobulin-like polypeptide encoded by the polynucleotide molecule described herein. Preferably, the immunoglobulin-like polypeptide binds to a tumor associated antigen, e.g., TAG-72, a viral or bacterial antigen, a lymphocyte associated antigen, or a cell adhesion molecule or ligand thereof. When the immunoglobulin-like polypeptide binds to TAG-72, a preferred embodiment comprises the hypervariable regions of CC49, and may comprise human CH2 and CH3 $F_c$ domains, e.g., the immunoglobulin-like polypeptide designated herein as $SCA\Delta C_L C_H 1$.

The invention also provides a method for treating a carcinoma or a metastasis thereof. A patient afflicted with the carcinoma or metastasis is administered an effective amount of an immunoglobulin-like polypeptide sufficient to inhibit the growth and proliferation of the carcinoma cells. When the tumor expresses the tumor associated antigen TAG-72, the variable regions of the immunoglobulin-like polypeptide are preferably comprised of at least the hypervariable regions of CC49.

In another aspect the invention provides a method for treating a carcinoma by introducing an expression vector which comprises a polynucleotide molecule which encodes the immunoglobulin-like polypeptide into tumor-infiltrating lymphocytes which have obtained from the patient. Upon expression of the immunoglobulin-like polypeptide, the tumor-infiltrating lymphocytes are returned to the patient and act to inhibit the tumor cells.

DESCRIPTION OF THE SPECIFIC EMBODIMENTS

The present invention provides an immunoglobulin-like molecule containing Fc functions while obviating the need for delivering two independent genes in a single cell. The invention also circumvents the problem of inefficient assembly of differentially expressed heavy and light chains into a functional immunoglobulin molecule. The present invention provides a molecule with a covalently linked $V_H$, $V_L$, and Fc domains encoded in a single gene. This immunoglobulin-like molecule takes advantage of the fact that single-chain Fv proteins can retain the antigen-binding specificity and affinity of the original antibody, despite covalent linkage between the $V_H$ and the $V_L$ domains. In addition, the effector functions of the $C_H$ domain (e.g., of human IgG1) can be maintained in a chimeric molecule.

In an exemplary embodiment of the invention described herein, a single-gene-encoded immunoglobulin-like molecule is derived from a parental chimeric (mouse-human) monoclonal antibody. A dimeric molecule which comprises the variable domains of murine antibody and the Fc region of human IgG1 is secreted by the mammalian cell transfected with the construct containing the single gene. The dimeric immunoglobulin-like molecule retains the ADCC activity and the antigen-binding specificity of the chimeric monoclonal antibody. This immunoglobulin-like molecule offers therapeutic advantages, and, by virtue of being chimeric, induces little or no human anti-murine antibody response in human patients. The single-gene construct also permits the ex vivo transfection of cells for the delivery of a tumoricidal antibody to a tumor site for gene therapy.

The preparation of single polypeptide chain binding molecules of the Fv region, single-chain Fv molecules, is described in U.S. Pat. No. 4,946,778, which is incorporated herein by reference. In the present invention, single-chain Fv-like molecules are synthesized by encoding a first variable region of the heavy or light chain, followed by one or more linkers to the variable region of the corresponding light or heavy chain, respectively. The selection of appropriate linker(s) between the two variable regions is described in U.S. Pat. No. 4,946,778. An exemplary linker described herein is $(Gly-Gly-Gly-Gly-Ser)_2$. The linker is used to convert the naturally aggregated but chemically separate heavy and light chains into the amino terminal antigen binding portion of a single polypeptide chain, wherein this antigen binding portion will fold into a structure similar to the original structure made of two polypeptide chains and thus retain the ability to bind to the antigen of interest.

Figure 2:
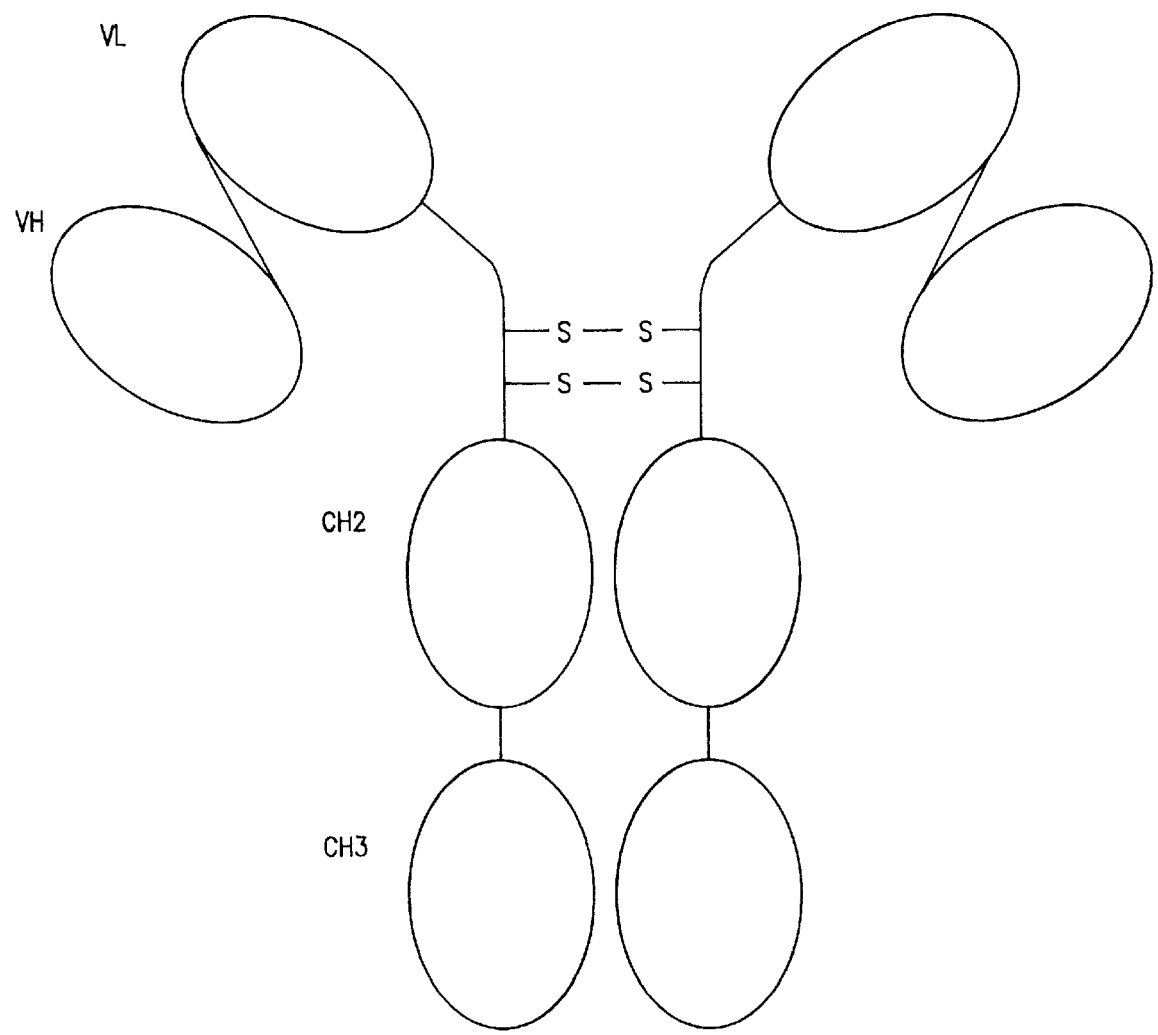
FIG. 2 shows a schematic diagram of the dimeric protein $SCA\Delta C_L C_H 1$.

The nucleotide sequences encoding the variable regions of the heavy and light chains, joined by a sequence encoding a linker, are joined to a nucleotide sequence encoding antibody constant regions. The constant regions are those which permit the resulting polypeptide to form interchain disulfide bonds to form a dimer, and which contain desired effector functions, such as the ability to mediate antibody-dependent cellular cytotoxicity (ADCC). For an immunoglobulin-like molecule of the invention which is intended for use in humans, the constant regions will typically be substantially human to minimize a potential anti-human immune response and to provide approbate effector functions. Manipulation of sequences encoding antibody constant regions is described in the PCT publication of Morrison and Oi, WO 89/07142, which is incorporated herein by reference. In preferred embodiments, the CH1 domain is deleted and the carboxyl end of the second variable region is joined to the amino terminus of CH2 through the hinge region. The Cys residue of the hinge which makes a disulfide bond with a corresponding Cys of the light chain, to hold the heavy and light chains of the native antibody molecule, can be deleted or, preferably, is substituted with, e.g., a Pro residue or the like. Thus, the Cys residues which remain in the hinge region are those which provide disulfide linkage between two heavy chains. A schematic diagram of the resulting immunoglobulin-like dimeric molecule is shown in FIG. 2.

Thus, the isolated polynucleotide molecule codes for a single chain immunoglobulin-like polypeptide having binding affinity for a selected antigen. The immunoglobulin-like polypeptide comprises a first polypeptide comprising the binding portion of the light chain variable region of an antibody or substantially all of the light chain variable region; a second polypeptide comprising the binding portion of the heavy chain variable region of an antibody or substantially all of the variable region; at least one peptide linker linking said first and second polypeptides; and a third polypeptide comprising the constant region domains CH2 and CH3. The peptide linker is not necessarily from an antibody, and links the first and second polypeptides into the single chain polypeptide. The single chain polypeptide encoded by the polynucleotide molecule may comprise, in sequence: (i) an N-terminal polypeptide from the light chain variable region of an antibody; (ii) a peptide linker; (iii) a C-terminal polypeptide from the heavy chain variable region of an antibody; and (iv) a heavy chain constant region domain. Alternatively, the elements may be arranged in the sequence: (i) an N-terminal polypeptide from the heavy chain variable region of an antibody; (ii) a peptide linker; (iii) a C-terminal polypeptide from the heavy chain variable region of an antibody; and (iv) the heavy chain constant region domain. In preferred embodiments the heavy chain constant region domains are the CH2 and CH3 domains, and are preferably substantially human when the polypeptide is intended for use in humans.

To prepare the polynucleotide sequence of the single-gene encoded immunoglobulin-like molecule, it is possible to utilize synthetic DNA by synthesizing the entire sequence de novo. Alternatively, it is possible to obtain cDNA sequences coding for certain preserved portions of the variable light and heavy chain regions of the desired antibody, and splice them together, by means of the necessary sequence coding for the peptide linker, which sequences are further spliced to sequences encoding the desired heavy chain constant region domains.

The resulting sequences can be amplified by utilizing well known cloning vectors and well known hosts. Furthermore, the amplified sequence, after checking for correctness, can be linked to promoter and terminator signals, inserted into appropriate expression vectors, and transformed into hosts such as eukaryotic hosts, preferably mammalian cells which are capable of correcting processing the immunoglobulin-like chains, e.g., the SP2/0-Ag14 murine myeloma cell line. Bacteria, yeasts (or other fungi) or other mammalian cells may also be utilized. Upon expression the single- chain binding protein is allowed to refold in physiological solution, at appropriate conditions of pH, ionic strength, temperature, and redox potential, and assemble as dimers to form the dimeric immunoglobulin-like molecules. These molecules can then be purified by standard separation procedures. These include chromatography in its various different types, e.g., affinity chromatography, known to those of skill in the art.

The thus obtained purified single-chain immunoglobulin-like binding protein can be utilized by itself, in detectably labelled form, in immobilized form, or conjugated to drugs or other appropriate therapeutic agents, in diagnostic, imaging, biosensors, purifications, and therapeutic uses and compositions. Essentially all uses envisioned for antibodies or for variable region fragments thereof can be considered for the molecules of the present invention.

Generally, it is possible to utilize the cDNA sequences obtained from the light and heavy chains of the variable region of the original antibody as a starting point. These sequences can then be joined by means of genetic linkers coding for the peptide linker. As noted above, the genetic sequence can be entirely synthesized de novo or fragments of cDNA can be linked together with the synthetic linkers.

A large source of hybridomas and their corresponding monoclonal antibodies are available for the preparation of sequences coding for the H and L chains of the variable region. Most variable regions of antibodies of a given class are in fact quite constant in their three dimensional folding pattern, except for certain specific hypervariable loops. Thus, to choose and determine the specific binding specificity of the single-gene encoded immunoglobulin-like binding protein of the invention it becomes necessary only to define the protein sequence (and thus the underlying genetic sequence) of the hypervariable region. The hypervariable region will vary from binding molecule to molecule, but the remaining domains of the variable region will remain constant for a given class of antibody.

Source mRNA can be obtained from a wide range of hybridomas. See for example the *ATCC Catalogue of Cell Lines and Hybridomas*, 7th ed., 1992, American Type Culture Collection, 12301 Parklawn Drive, Rockville, Md. 20852. Hybridomas secreting monoclonal antibodies reactive with a wide variety of antigens are listed therein, are available from the collection, and usable in the invention. Of particular interest are hybridomas secreting antibodies which are reactive with tumor associated antigens, viral antigens, bacterial and fungal antigens, lymphocyte and cell adhesion antigens, and the like. These cell lines and others of similar nature can be utilized to copy mRNA coding for the variable region or hypervariable region or one may determine amino acid sequence from the monoclonal antibody itself. The specificity of the antibody to be engineered will be determined by the original selection process. The class of antibody can be determined by criteria known to those skilled in the art, and one need only replace the sequences of the hypervariable regions (or complementary determining regions). The replacement sequences will be derived from either the amino acid sequence or the nucleotide sequence of DNA copies of the mRNA.

A genetic construct comprising the isolated polynucleotide molecule of the single-gene-encoded immunoglobulin-like molecule is typically placed under the control of a single promoter. A variety of promoters and transcriptional enhances suitable for controlling and/or enhancing immunoglobulin expression are available, e.g., the human cytomegalovirus promoter, etc. DNA constructs for expressing human immunoglobulins are described in EP patent publication EP 0 314 161, incorporated herein by reference. The expression of the immunoglobulin-like molecule can also be placed under control of other regulatory sequences which are known to those skilled in the art.

Preferred host cells are mammalian cells, grown in vitro in tissue culture, or in vivo in animals. Mammalian cells provide post translation modifications to immunoglobulin protein molecules including correct folding or glycosylation at correct sites. Mammalian cells useful as hosts include cells of fibroblast origin such as VERO or CHOK1, or cells of lymphoid origin, such as the hybridoma SP2/0-AG14 or the myeloma P3×63Sg8, and their derivatives. Transfection can be by electroporation, calcium phosphate coprecipitation, protoplast fusion, or microinjection. Following transfection the cells are incubated in nonselective medium or selective medium. After a sufficient time for cell outgrowth, the supernatants are tested for the presence of the desired immunoglobulin-like molecule by any of a variety of techniques, e.g., ELISA or the like.

The expressed and refolded single-gene-encoded immunoglobulin-like binding proteins of the invention can be labelled with detectable labels such as radioactive atoms, enzymes, biotin/avidin labels, chromophores, chemiluminescent labels, and the like for carrying out standard immunodiagnostic procedures. These procedures include competitive and immunometric (or sandwich) assays. See., e.g., U.S. Pat. No. 4,376,110, incorporated herein by reference. These assays can be utilized for the detection of antigens in diagnostic samples. In competitive and/or sandwich assays, the binding proteins of the invention can also be immobilized on such insoluble solid phases as beads, test tubes, or other polymeric materials. For imaging procedures, the binding molecules of the invention can be labelled with opacifying agents, such as NMR contrasting agents or X-ray contrasting agents. Methods of binding labelling or imaging agents or proteins as well as binding the proteins to insoluble solid phases are well known in the art. The dimeric immunoglobulin-like proteins can also be used for therapy when labeled or coupled to enzymes or toxins, and for purification of products, especially those produced by the biotechnology industry, or can be used unlabeled. Thus, uses for the single-gene-encoded immunoglobulin-like binding proteins of the invention include both in vitro diagnostic assays and in vivo diagnostic assays (diagnostic imaging). Such uses are discussed in detail in co-pending U.S. application Ser. No. 07/547,336, which is incorporated herein by reference.

The single-gene-encoded immunoglobulin-like binding proteins find use as in vivo or ex vivo therapeutic agents. For in vivo therapeutic use, the proteins are administered, typically formulated with excipients and carriers as a pharmaceutical agent, to a patient in need thereof, e.g., one who is suffering from or disposed to disease associated with an antigen to which the immunoglobulin-like polypeptide binds. These antigens include viral (e.g., retroviral, hepatitis B and C antigens) and bacterial antigens, tumor-associated antigens (e.g., TAG-72, p97, CEA, MAGE antigens, etc.), cellular adhesion molecules and their respective ligands (e.g., the CD11/CD18 antigen family; see PCT WO094/02175, incorporated herein by reference), and the like. The single-gene-encoded immunoglobulin-like binding proteins are formulated and administered to the patient in need thereof in an amount sufficient to effect the desired response, typically regression or inhibition of the tumor or bacterial cells, or virus-infected cells, and inhibit inflammation or tissue reperfusion injury. The amounts necessary will typically be less than those necessary with the parental monoclonal antibody to achieve the same effect.

Another aspect of the single-gene construct encoding the immunoglobulin-like molecule is that the construct can be efficiently and conveniently introduced into cultured human tumor-infiltrating lymphocytes (TILs). Since TILs propagate rapidly, they can be expanded and reintroduced into the host for tumor gene therapy. Delivery of the tumoricidal antibody to the tumor site will be facilitated by the preferential localization of TILs at the tumor. Introduction of cloned genes into TILs via retroviral vector has been demonstrated (Kasid et al., Proc. Natl. Acad. Sci. USA 87:473–477 (1990)), and it has recently been demonstrated that a T-cell line can secrete chimeric monoclonal antibodies (Tsang et al., J. Immunother. 13:143–152 (1993)). Retroviral vectors are described in PCT publication WO 93/04167 and GB 2,269, 175, incorporated herein by reference. The single-gene approach is thus particularly attractive for ex vivo transfection of cells from patients for certain gene-therapy modalities, not only for cancer but also for a range of diseases in which immunotherapeutic approaches are possible.

The following examples are offered by way of illustration, not by way of limitation.

EXAMPLE I

Generation of a Single-Gene Encoding an Immunoglobulin-Like Molecule

This Example describes the generation of a single-gene-encoded immunoglobulin-like molecule, designated SCAΔCLCH1. The dimeric molecule is derived from chimeric monoclonal antibody CC49 in that it comprises the variable domains of the murine CC49, $V_H$ and $V_L$, and the Fc region of human IgG1. It is secreted from the transfectoma and retains the ADCC activity and the antigen-binding specificity of the chimeric monoclonal antibody CC49. The parental CC49 molecule is described in U.S. application Ser. No. 07/547,336, which is incorporated herein by reference in its entirety.

Figure 1:
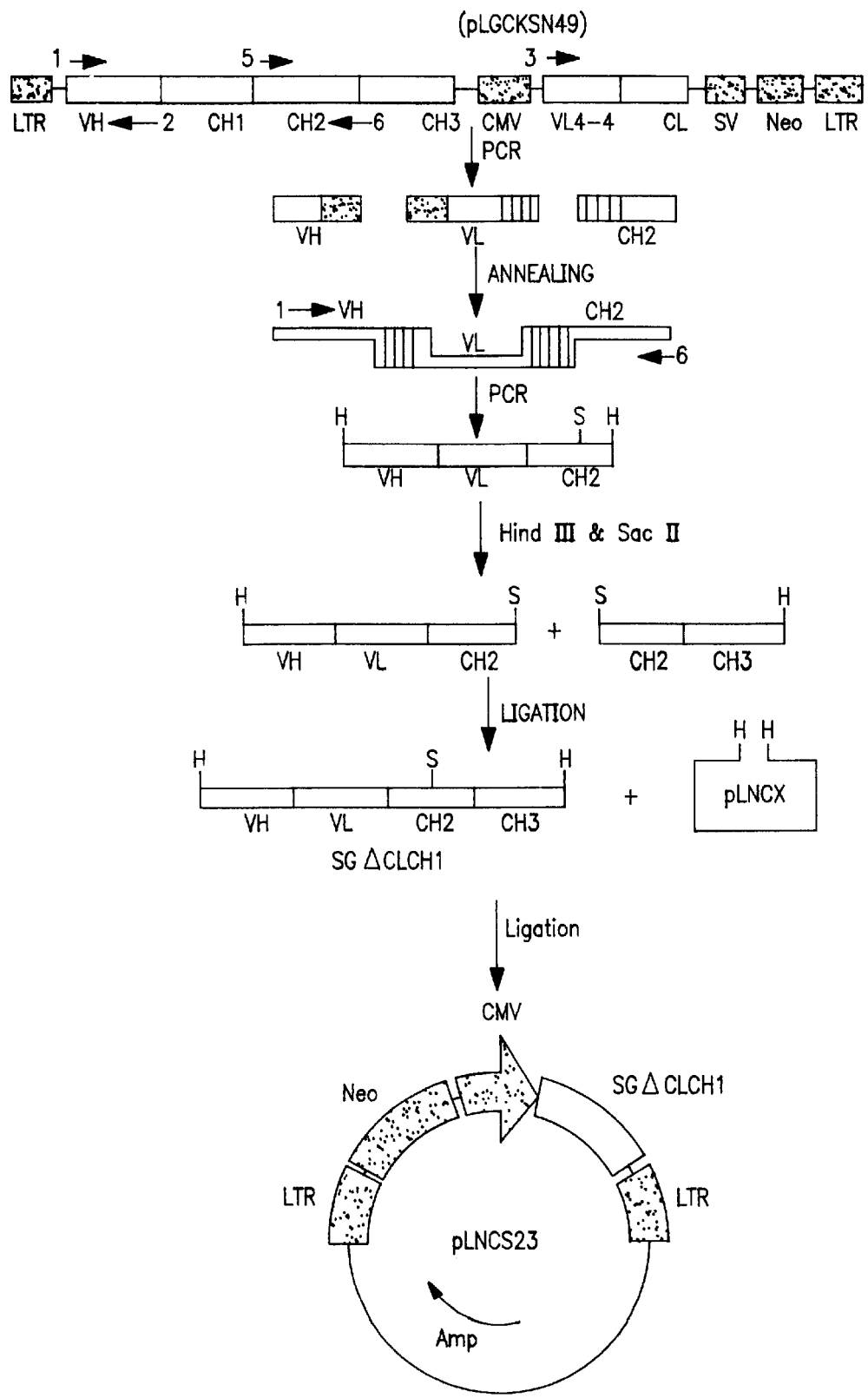
FIG. 1 shows a schematic flow sheet for the generation of the single gene $SCA\Delta C_L C_H 1$ of mAb CC49 and its expression construct. The template DNA (pLGCKSN49), the final single gene ($SG\Delta C_L C_H 1$), the expression construction (pLNCS23), and a flow sheet of steps leading from the template DNA to the single-gene construct are shown schematically. CMV, human cytomegalovirus promoter; LTR, long terminal repeat; Neo, neomycin-resistance gene; Am;, ampicillin-resistance gene; SV, simian virus 40 promoter; S, Sac II; H, HindIII.

The single-gene construct $SG\Delta C_L C_H 1$, encoding CC49 $V_H$ and $V_L$ and the entire Fc region of the human γ1 heavy chain, is shown in FIG. 1 and the immunoglobulin-like dimeric molecule is schematically presented in FIG. 2. The design of the single-chain monomeric protein included a covalent linkage of the carboxyl terminus of the $V_H$ domain and the amino end of the $V_L$ domain through a (Gly-Gly-Gly-Gly-Ser)$_3$ peptide linker (Huston et al., Proc. Natl. Acad. Sci. USA 85:587–588 (1988)). Also, the carboxyl end of $V_L$ and the amino end of the $C_H 2$ were joined through the hinge region. In this construct, $Cys^{220}$ of the genetic hinge was replaced by a proline residue, while $Cys^{226}$ and $Cys^{229}$ were retained in the functional hinge. $Cys^{220}$ makes a disulfide bond with $Cys^{214}$ of the k light chain to hold the heavy and light chains of the native antibody together. Cysteine residues 226 and 229 provide disulfide linkage between two heavy chains. The changes were brought about by primer-induced mutagenesis, as described below. Site-directed mutagenesis via amplification oligonucleotides was also used to destroy the Sac II site from the CC49 $V_L$ exon.

The procedure used to generate the construct is presented schematically in FIG. 1. The $V_H$ and $V_L$ regions of CC49 and human γ1 $C_H 2$ regions were amplified by using the construct pLGCKSN49 as the template. pLGCKSN49 was generated from the retroviral vector pLNCX by insertion of a BamHI fragment encoding chimeric heavy chain of CC49 downstream from the long terminal repeat of Moloney murine sarcoma virus and insertion of a DNA fragment encoding the chimeric light chain of CC49 at the HindIII site downstream from the human cytomegalovirus promoter.

The sequences of the oligonucleotide primers synthesized for DNA amplifications were as follows:

[SEQ ID No:1]
(5' $V_H$, coding), 5'-TCGCAC*AAGCTT*TAACCATGGAATGGAGCTGG-3';

[SEQ ID No:2]
(3'$V_H$ noncoding),
5'-CCTCCCGAGCCACCGCCTCCGCTGCCTCCGCCT
CCTGAGGAGACGGTGACTGAGG-3';

[SEQ ID No:3]
(5'$V_L$ coding),
5'-GCAGCGGAGGCGGTGGCTCGGGAGGCGGAGGCTC
GGACATTGTGATGTCACAGTCTC-3';

[SEQ ID No:4]
(3' $V_L$, noncoding),
5'-GTCAggAGATTTGGGCTCgGCGGCCCGTTTCAG
CACCAG-3';

[SEQ ID No:5]
(5'$C_H$2, coding), 5'-GGCCGCcGAGCCCAAATCTccTGACAAAACTCAC
ACATGCCC-3';

[SEQ ID No:6]
(3'$CH_2$, noncoding), 5'-GGGGCT*AAGCTT*AGGCTTTGGAGATGGTTTT
CTC-3'.

The overlapping complementary sequences are underlined, and the nucleotides which mismatch with the template are in lowercase letters. The sequences recognized by the restriction endonucleases are in italics. Primers SEQ ID No:2 and 3 had a 25-bp complementing overlap and each encoded a part of the (Gly$_4$-Ser)$_3$ linker peptide. Similarly primers SEQ ID No:4 and 5 carried 25-bp overlapping sequences, and together they encoded the carboxyl end of the $V_L$ and the amino end of the hinge region. Oligonucleotides SEQ ID No:4 and 5 were instrumental in the site-directed mutagenesis mentioned earlier. A single molecule encompassing all three amplified fragments was generated by recombinant PCR using the three amplified DNA fragments as templates and oligonucleotides SEQ ID No:1 and 6 as 5' and 3' primers. The DNA amplification was carried out essentially as described in Horan Hand et al., *Cancer Immunol. Immunother.* 35:165–174 (1992), incorporated herein by reference. The final product, of ~1170 bp, was treated with HindIII. Generation of the molecule carrying the entire Fc region was facilitated by a Sac II site located ~145 bp upstream from the stop codon. By taking advantage of the enzyme site, an ~1030-bp HindIII-Sac II fragment was generated from the 1170-bp HindIII fragment. It was ligated to an ~480-bp Sac II-HindIII DNA fragment lifted from the sequence encoding the C region of the human γ1 chain present in the original template. The latter fragment encoded the $C_H$3 domain and the carboxyl end of the $C_H$2 domain. A 1520-bp HindIII fragment carrying $V_H$, $V_L$, and the entire Fc region thus generated was finally inserted in the pLNCX vector (Tsang et al., *J. Immunother.* 13:143–152 (1993)) at the HindIII site located downstream from the cytomegalovirus promoter. The resulting expression construct, pLNCS23, is shown in FIG. 1.

The eukaryotic expression construct was introduced into SP2/0-Ag14 mouse myeloma cells by electroporation (Slavin-Chiorini et al., *Int. J. Cancer* 53:97–103 (1993)) with the Cell-Porator system (GIBCO/BRL). After electroporation, transfectants were selected in complete Dulbecco's modified Eagle's medium containing G418 (50% effective) (GIBCO/BRL) at 1.5 mg/ml.

After 2 weeks of selection, tissue culture supernatants from 20 wells were assayed by ELISA. To carry out ELISA, individual wells of the 96-well polyvinyl microtiter plates were coated with 20 μg of protein extract of either TAG-72-negative A375 human melanoma xenografts. The remainder of the assay was performed as described (Horan Hand et al., *Cancer Immunol. Immunother.* 35:165–174 (1992)). Fourteen well were positive for reactivity to the LS-174T human colon carcinoma cells, which express TAG-72 antigen. None of the supernatants showed reactivity to the TAG-72-negative A375 human melanoma.

Cells from the well which showed highest reactivity to TAG-72 were adapted to grow in serum and protein-free medium for further characterization. SCAΔ$C_L C_H$1 was purified from the protein-free culture supernatant by protein G column chromatography. Approximately 4μg of antigen-binding protein was produced per ml of the culture fluid.

For purification and physical characterization the SCAΔCLCH1 protein was purified from tissue culture supernatant of the producer clone grown in protein-free hybridoma medium (PFHM-II; GIBCO/BRL) by protein G affinity chromatography. Recombinant protein G-agarose was purchased from GIBCO/BRL and purification was carried out according to the supplier's recommendation. The eluted material from the column was concentrated with a Centricon 30 microconcentrator (Amicon). The concentrated material was analyzed on precast SDS/10–27% polyacrylamide Tris glycine gels (Novex System, San Diego) with and without 2-mercaptoethanol. The proteins were visualized by staining with Coomassie blue R250.

Figure 3:
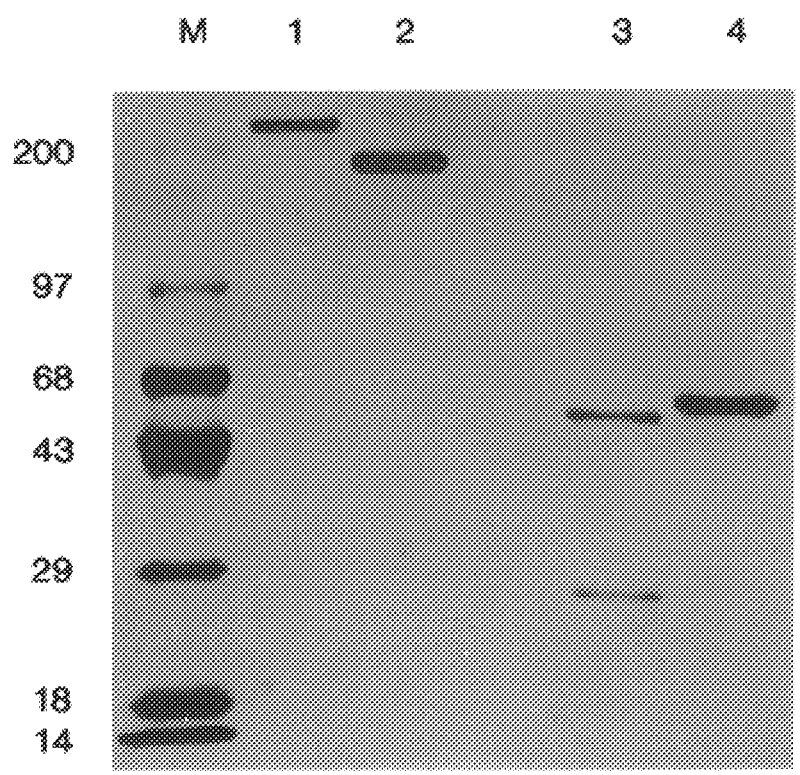
FIG. 3 shows the SDS/PAGE analysis of protein G-purified $SCA\Delta C_L C_H 1$ under nonreducing (lanes 1 and 2) and reducing (lanes 3 and 4) conditions. Lanes: M, markers (sizes in kilodaltons at left); 1 and 3, chimeric CC49; 2 and 4, protein G column purified $SCA\Delta C_L C_H 1$ secreted by transfected SP2/0 cells.

The size and purity of the protein G column-purified material were determined by SDS/PAGE analysis, as shown in FIG. 3. For comparison, chimeric CC49 was included in the analysis. Under reducing conditions, the SDS/PAGE profile of chimeric CC49 showed two distinct bands: a light-chain band of 25–27 kDa and a heavy-chain band of 50–55 kDa (lane 3). In contrast, only one distinct band was seen for SCAΔ$C_L C_H$1 band showed slower migration than the heavy chain of chimeric CC49.The molecular mass of the reduced protein was ≈60 kDa. Under nonreducing conditions, both chimeric CC49 and SCAΔ$C_L C_H$1 appeared as individual single bands (lanes 1 and 2). The molecular masses of chimeric CC49 and SCAΔ$C_L C_H$1 appeared significantly higher than expected. The presence of the intact disulfide bonds in these proteins may account for their aberrant migration. Gel filtration HPLC profiles of chimeric CC49 and SCAΔ$C_L C_H$1 showed peaks consistent with molecular masses of 165 and 120 kDa, respectively. The apparent size of SCAΔ$C_L C_H$1 is consistent with the estimated molecular mass of 115 kDa.

Unlike a single-chain Fv molecule, the single-chain protein of ≈60 kDa assembles into a functional dimeric molecule, SCAΔ$C_L C_H$1, of ≈120 kDa. The disulfide bridges between the monomers are most likely made by Cys$^{226}$ and Cys$^{229}$, which are retained in the hinge region (FIG. 2). Cys$^{220}$ of the genetic hinge makes a disulfide bond with Cys$^{214}$ of the human κ light chain to hold the heavy and the light chains of the native antibody together. Since this immunoglobulin-like molecule is deficient in its $C_κ$ region, Cys$^{220}$ was replaced with a proline residue, lest this cysteine residue interfere with proper assembly. The substitution did not seem to affect antigen binding affinity or the effector function of the molecule.

Thus, the inefficiencies attendant with transfection and assembly of the heavy and light chains into a functional immunoglobulin have been circumvented by constructing a single gene encoding all the domains essential for making the antigen binding site and the human IgG1 Fc region. This single gene, SCAΔ$C_L C_H$1, encodes a single-chain protein, SCAΔ$C_L C_H$1, in which $V_H$ and $V_L$ domains of CC49 are covalently joined together through a short linker peptide. The carboxyl end of the $V_L$ domain of this resulting sFv fragment is in turn linked to the amino terminus of the human IgG1 Fc domain through the hinge region.

EXAMPLE II

Relative Antigen Binding Affinity of Single-Gene-Encoded Immunoglobulin-Like Molecule This Example demonstrates via competition assays that the single-gene-encoded immunoglobulin-like CC49 SCAA$C_L C_H$1 possesses almost the same binding affinity for the TAG-72 antigen as the parental murine monoclonal antibody CC49.

Competition assays were performed to compare the binding of CC49 SCAA$C_L C_H$1 murine monoclonal antibody CC49, and chimeric CC49 to the protein extracts of the TAG-72-positive LS-174T xenografts. Unlabeled immunoglobulins were used to compete with the biotinylated murine CC49 for binding to antigen. The competition assays were performed as described (Horan Hand et al., Cancer Immunol. Immunother. 35:165–174 (1992)), except that biotinylated murine CC49 was used instead of radiolabeled antibody. After the final step, the absorbance was read at 490-nm wavelength. Percent binding is the ratio of the observed absorbance to the total absorbance times 100. Total absorbance was obtained by doing the assay without the competitor. Percent inhibition was obtained by subtracting the percent binding from 100.

Figure 4:
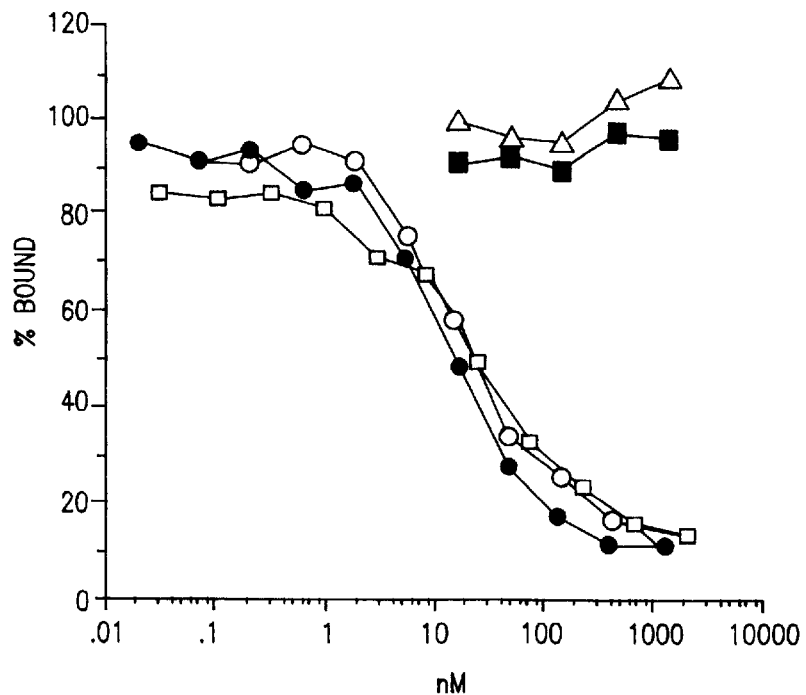
FIG. 4 shows competition assay for binding of $SCA\Delta C_L C_H 1$ (□), murine monoclonal antibody CC49 (●), chimeric CC49 (○), MOPC-21 (■), and human IgG1 (Δ) were used in increasing concentrations to compete for the binding of biotinylated murine monoclonal antibody CC49 to the protein extract of the TAG-72-positive LS-174T human colon carcinoma.

The results showed that all three species of mAb CC49 competed completely and the slopes of the competition curves of the three antibodies were similar (FIG. 4). Approximately 25 nM SCAA$C_L C_H$1, 15 nM murine monoclonal antibody, and 25 nM chimeric CC49 were required for 50% inhibition of the binding of biotinylated murine CC49 to TAG-72. Control antibodies (MOPC-21 and human IgG1) did not compete with the biotinylated antibody.

Thus, in contrast to many single-chain Fv molecules, which have lower Ka values than intact IgG, and in particular the single-chain Fv of CC49, the results of the competition assay (FIG. 4) demonstrate that SCAA$C_L C_H$1 has almost the same affinity for TAG-72 as does the murine mAb CC49. The deficiency of the $C_H$1 domain in SCAA$C_L C_H$1 did not affect its antigen binding affinity, but for some other antigen-antibody systems the absence of the $C_H$1 domain may alter the antigen binding affinity. The loss of the $C_H$1 domain may confer a certain rigidity on the binding site or may affect the spacing of binding sites crucial for antigen binding affinity.

EXAMPLE III

CC49 SCAA$C_L C_H$1 Mediates ADCC

This Example demonstrates that the single-gene-encoded immunoglobulin-like dimeric CC49 SCAA$C_L C_H$1 with human effector cells, mediates antibody-dependent cellular cytotoxicity against human endometrial carcinoma cells and thus is of therapeutic utility.

Chimeric monoclonal antibody B72.3 (γl) participates with human effector cells in mediating ADCC against carcinoma cell lines that express TAG-72 on their cell surface in vitro (Primus et al., Cancer Immunol. Immunother. 31:349–357 (1990)), unlike the murine mAb B72.3 (γl). Exposure of human effector cells to IL-2 augments this antibody-mediated lysis of the cultured target cells (Primus et al., Cancer Immunol. Immunother. 31:349–357 (1990)).

Figure 5A:
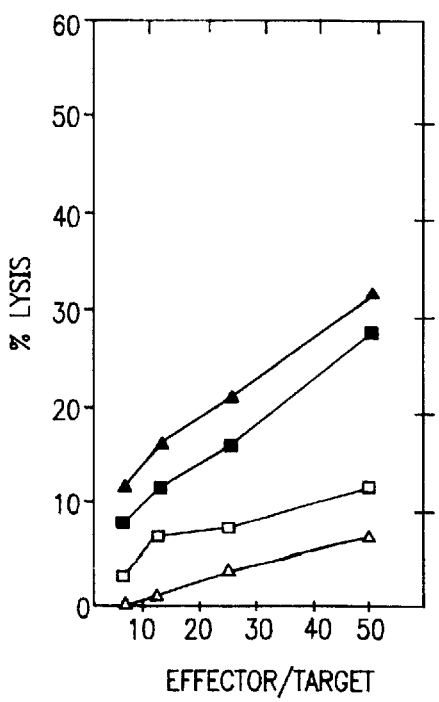
FIG. 5A and 5B show the ADCC of $SCA\Delta C_L C_H 1$, where a 24-hr $^{111}$In-release assay was performed using untreated (FIG. 5A) and IL-2 (100 units/ml)-treated (FIG. 5B) human effector cells. Effector cells and $^{111}$In-labeled KLE-B human endometrial carcinoma target cells were used at different effector/target cell ratios in the presence of $SCA\Delta C_L C_H 1$ (■), chimeric CC49 (▲), murine CC49 (□), and human IgG1 (Δ)
Figure 5B:
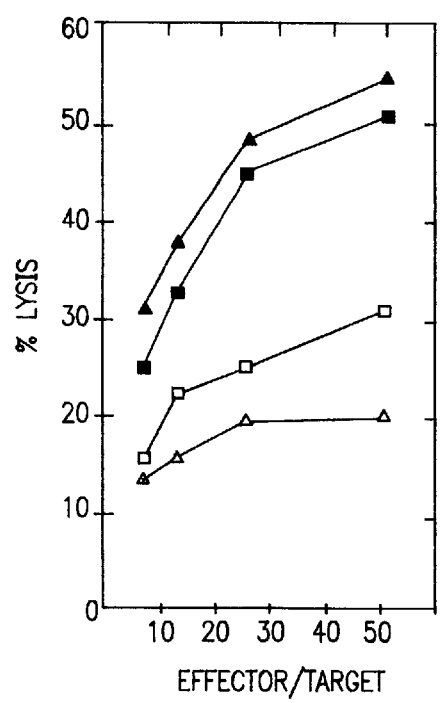

The ADCC activity of CC49 SCAA$C_L C_H$1 and chimeric CC49 (γ) were compared in a 24-hr $^{111}$In-release assay using KLE-B, a human endometrial carcinoma cell line which constitutively expresses the TAG-72 antigen. Human peripheral blood mononuclear cells used as effectors were cultured with or without recombinant human IL-2 (100 units/ml) for 24 hr. The remainder of the assay and calculation of percent lysis were as generally described in Hutzell et al., Cancer Res. 51:181–189 (1991), incorporated herein by reference. At each effector/target cell ratio, the ADCC activity of SCAA$C_L C_H$1 was similar to that of chimeric CC49 (FIG. 5A). At an effector/target cell ratio of 50, cell lysis mediated by chimeric CC49 and SCAA$C_L C_H$1 was 32% and 28%, respectively. The murine mAb CC49 and the irrelevant human IgG showed very low cytotoxicity. Exposure of the human effector cells to IL-2 (100 units/ml) substantially augmented the lytic potential of both chimeric CC49 and SCAA$C_L C_H$1. At the highest effector/target cell ratio, target cytolysis mediated by both molecules reached 50–55% (FIG. 5B). Thus, ADCC activity of SCAA$C_L C_H$1 is comparable to ADCC activity of chimeric CC49.

In addition to the single-chain protein SCAA$C_L C_H$1 comprising the $V_H$ and $V_L$ domains covalently joined through the Gly-Ser linker, with the carboxyl end of the $V_L$ domain linked to the amino terminus of the human γ1 Fc through a hinge region, other single-chain proteins with comparable activity have been constructed. For example, a second DNA construct encoded a single chain fusion protein which was secreted as a dimeric molecule (SCAA$C_H$1$C_L$-IL-2) of ~140 kDa. SCAA$C_H$1$C_L$-IL-2 was comprised of SCAA$C_H$1$C_L$ with an interleukin-2 molecule attached to the carboxyl end of its Fc region. A third single gene construct expressed a single-chain protein in which the carboxyl end of the constant region of the chimeric light chain and the amino terminus of the variable region of the chimeric heavy chain were joined through a gly-ser linker peptide. An ~160 kDa homodimer of this single chain, SCAcCC49, is secreted into the culture medium of its transfectoma. All three single chain immunoglobulins competed with CC49 for binding to TAG-72. The ADCC activity of the single chain antibodies was comparable to the cytotoxic activity of the chimeric MAb CC49. The fusion protein SCAA$C_H$1$C_L$-IL-2 retained the biological activity of the human interleukin-2, as detected by cell proliferation assay.

The expression, purification, and characterization of the SCAA$C_L C_H$1 described in the foregoing Examples demonstrates that a recombinant single gene can be expressed in a mammalian cell to result in subsequent secretion of a functional immunoglobulin-like molecule. The molecule, generated by a convenient single-step transfection of the mammalian cell, shows fidelity to the antigen-binding specificity of the parental antibody and also retains its ability to mediate ADCC, a function that resides in the Fc region. This single gene approach for the generation of a functional immunoglobulin-like molecule can easily be applied to drive single-chain molecules of native therapeutic utility from other murine anti-tumor antibodies. A sFv construct flanked with appropriate restriction endonuclease sites can be conveniently inserted in an expression cassette carrying the human Fc region. These immunoglobulin-like molecules can serve as therapeutic and diagnostic reagents against a wide range of human carcinomas and other diseases.

Although the foregoing invention has been described in some detail by way of illustration and example for purposes of clarity of understanding, it will be obvious that certain changes and modifications may be practiced within the scope of the appended claims.

What is claimed is:

1. An isolated polynucleotide molecule which codes for a single chain immunoglobulin-like polypeptide having binding affinity for an antigen, said polypeptide consisting essentially of:
    (a) a first polypeptide comprising the binding portion of the light chain variable region of an antibody;
    (b) a second polypeptide comprising the binding portion of the heavy chain variable region of an antibody;
    (c) at least one peptide linker linking said first and second polypeptides (a) and (b); and
    (d) a third polypeptide consisting essentially of heavy chain constant region domains wherein $CH_1$ is deleted and an amino end of $CH_2$ is joined to a carboxyl end of the first polypeptide through a hinge region, wherein the first cysteine of the hinge region, said cysteine making a disulfide bond with a light chain, is deleted or substituted with an amino acid, and wherein the second cysteine and the third cysteine of the hinge region provide interchain disulfide linkage between two heavy chain constant regions thereby forming a single gene encoded single chain polypeptide having binding affinity for said antigen and capable of forming an immunoglobulin-like dimer with constant region functions, wherein the single-chain immunoglobulin-like polypeptide binds to both a TAG-72 and a LS174T antigen, and wherein the single-chain immunoglobulin-like polypeptide specifically binds to an epitope specifically bound by CC49 (ATCC CRL 9459).

2. The polynucleotide molecule of claim 1, wherein the constant region function is mediation of antibody-dependent cellular cytotoxicity against cells which express the antigen of interest.

3. The polynucleotide molecule of claim 1 wherein said peptide linker (c) is not from an antibody.

4. The polynucleotide molecule of claim 1 wherein said single chain polypeptide comprises one linker linking said first and second polypeptides (a) and (b) into said single chain.

5. The polynucleotide molecule of claim 3 wherein said single chain polypeptide comprises in sequence;
    (i) an N-terminal polypeptide from the light chain variable region of an antibody;
    (ii) a peptide linker;
    (iii) a C-terminal polypeptide from the heavy chain variable region of an antibody; and
    (iv) a heavy chain constant region domain.

6. The polynucleotide molecule of claim 3 wherein said single chain polypeptide comprises in sequence:
    (i) an N-terminal polypeptide from the heavy chain variable region of an antibody;
    (ii) a peptide linker;
    (iii) a C-terminal polypeptide from the heavy chain variable region of an antibody; and
    (iv) a heavy chain constant region domain.

7. The polynucleotide molecule of claim 3 wherein said heavy chain constant region domain comprises the CH2 and CH3 domains.

8. The polynucleotide molecule of claim 7 wherein said heavy chain constant region domains are human.

9. A replicable cloning or expression vehicle comprising the polynucleotide molecule of claim 1.

10. The vehicle of claim 9 which is a plasmid.

11. A host cell transformed with the vehicle of claim 9.

12. The host cell of claim 11 which is a mammalian cell, a bacterial cell, a yeast cell or other fungal cell.

13. A mammalian host cell according to claim 12 which is a myeloma cell line.

14. A method of producing a single chain immunoglobulin-like polypeptide having binding affinity for an antigen and capable of forming a dimer, said polypeptide comprising (a) a first polypeptide comprising the binding portion of the light chain variable region of an antibody; (b) a second polypeptide comprising the binding portion of the heavy chain variable region of an antibody; (c) at least one peptide linker linking said first and second polypeptides (a) and (b); and (d) a third polypeptide consisting essentially of heavy chain constant region domains wherein $CH_1$ is deleted and an amino end of $CH_2$ is joined to a carboxyl end of the first polypeptide through a hinge, wherein the first cysteine of the hinge, said cysteine making a disulfide bond with a light chain region of $CH_2$, is deleted or substituted with an animo acid, and wherein the second cysteine and the third cysteine of the hinge region provide interchain disulfide linkage between two heavy chain constant regions thereby forming a single-gene encoded single chain polypeptide having binding affinity for said antigen and capable of forming an immunoglobulin-like dimer with constant region functions, said method comprising:
    (i) providing a polynucleotide molecule coding for said single chain immunoglobulin-like polypeptide;
    (ii) transforming a host cell with said polynucleotide molecule;
    (iii) expressing said polynucleotide molecule in said host;
    (iv) recovering said single chain immunoglobulin-like polypeptide having binding affinity for an antigen, wherein the single-chain immunoglobulin-like polypeptide binds to both a TAG-72 and a LS174T antigen, and wherein the single-chain immunoglobulin-like polypeptide specifically binds to an epitope specifically bound by CC49 (ATCC CRL 9459).

15. The method of claim 14 which further comprises purifying said recovered single chain immunoglobulin-like polypeptide having binding affinity for both a TAG-72 and a LS174T antigen and wherein the single-chain immunoglobulin-like polypeptide specifically binds to an epitope specifically bound by CC49 (ATCC CRL 9459).

16. The method of claim 14 wherein said host cell is a mammalian cell, a bacterial cell, yeast, or other fungal cell.

17. The method of claim 16 wherein said host cell is a myeloma cell line.

18. The polynucleotide molecule of claim 1, which encodes S C A Δ $C_L$ $C_H$ 1.

19. The immunoglobulin-like polypeptide encoded by the polynucleotide molecule of claim 1.

20. The immunoglobulin-like polypeptide of claim 19, which comprises the hypervariable regions of CC49 and human CH2 and CH3 $F_c$ domains.

21. The immunoglobulin-like polypeptide of claim 20, which is SCAΔ$C_L$$C_H$1.

22. The isolated polynucleotide of claim 1, wherein a nucleotide sequence encoding the hinge region comprises SEQ. ID NO: 5.

23. The isolated polynucleotide of claim 1, wherein a nucleotide sequence encoding the heavy chain variable region comprises SEQ. ID NO: 1.

24. The isolated polynucleotide of claim 1, wherein a nucleotide sequence encoding the light chain variable region comprises SEQ. ID NO: 3.

25. The polynucleotide according to claim 1 comprising SEQ. ID NO: 1, SEQ. ID NO: 3, and SEQ. ID NO: 5.

26. The polynucleotide according to claim 1 wherein the third polypeptide is derived from human IgG1 and wherein $Cys^{220}$ of the hinge region is replaced by proline.

27. The polynucleotide according to claim 1 wherein the first cysteine is replaced by proline.

28. The polynucleotide according to claim 1 wherein a nucleotide sequence encoding the first polypeptide comprises SEQ. ID NO: 3; a nucleotide sequence encoding the second polypeptide comprises SEQ. ID NO: 1; a nucleotide sequence encoding the linker (Gly-Gly-Gly-Gly-Ser)$_3$; and a nucleotide sequence encoding the $CH_2$ constant region domain comprises SEQ. ID NO: 5.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
TCGCACAAGC TTTAACCATG GAATGGAGCT GG                                32
```

( 2 ) INFORMATION FOR SEQ ID NO:2:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
CCTCCCGAGC CACCGCCTCC GCTGCCTCCG CCTCCTGAGG AGACGGTGAC TGAGG       55
```

( 2 ) INFORMATION FOR SEQ ID NO:3:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
GCAGCGGAGG CGGTGGCTCG GGAGGCGGAG GCTCGGACAT TGTGATGTCA CAGTCTC     57
```

( 2 ) INFORMATION FOR SEQ ID NO:4:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
GTCAGGAGAT TTGGGCTCGG CGGCCCGTTT CAGCACCAG                         39
```

( 2 ) INFORMATION FOR SEQ ID NO:5:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

-continued

GGCCGCCGAG CCCAAATCTC CTGACAAAAC TCACACATGC CC 42

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

GGGGCTAAGC TTAGGCTTTG GAGATGGTTT TCTC 34